United States Patent
Hill et al.

(10) Patent No.: US 6,916,880 B2
(45) Date of Patent: *Jul. 12, 2005

(54) MONOFILAMENT DENTAL TAPES WITH SUBSTANTIVE COATINGS

(75) Inventors: Ira D. Hill, Locust, NJ (US); Dale G. Brown, Wharton, TX (US)

(73) Assignee: International Tape Partners, LLC, Stafford, TX (US)

( * ) Notice: Subject to any disclaimer, the term of this patent is extended or adjusted under 35 U.S.C. 154(b) by 114 days.

This patent is subject to a terminal disclaimer.

(21) Appl. No.: 10/408,417

(22) Filed: Apr. 7, 2003

(65) Prior Publication Data

US 2003/0225196 A1 Dec. 4, 2003

Related U.S. Application Data

(63) Continuation of application No. 09/935,920, filed on Aug. 23, 2001, now Pat. No. 6,545,077.
(60) Provisional application No. 60/227,244, filed on Aug. 23, 2000, provisional application No. 60/227,255, filed on Aug. 23, 2000, and provisional application No. 60/227,433, filed on Aug. 23, 2000.

(51) Int. Cl.[7] ............................................. C08L 47/00
(52) U.S. Cl. ..................... 525/92 A; 525/92 R; 525/93; 525/88; 132/321; 132/323
(58) Field of Search ................................ 525/88, 92 R, 525/93, 92 A; 132/321, 323; 524/277

(56) References Cited

U.S. PATENT DOCUMENTS

| | | | |
|---|---|---|---|
| 3,800,812 A | 4/1974 | Jaffe | |
| 4,776,358 A | 10/1988 | Lorch | |
| 4,911,927 A | 3/1990 | Hill et al. | |
| 4,974,615 A | 12/1990 | Doundoulakis | |
| 5,033,488 A | 7/1991 | Curtis et al. | |
| 5,057,310 A | 10/1991 | Hill et al. | |
| 5,165,913 A | * 11/1992 | Hill et al. | ............... 424/49 |
| 5,209,251 A | 5/1993 | Curtis et al. | |
| 5,219,572 A | 6/1993 | Sivaramakrishnan et al. | |
| 5,220,932 A | 6/1993 | Blass | |
| 5,433,226 A | 7/1995 | Burch | |
| 5,479,952 A | 1/1996 | Zachariades et al. | |
| 5,503,842 A | 4/1996 | Fazan et al. | |
| 5,518,012 A | 5/1996 | Dolan et al. | |
| 5,538,667 A | 7/1996 | Hill et al. | |
| RE35,439 E | 2/1997 | Rosenberger | |
| 5,651,959 A | 7/1997 | Hill et al. | |
| 5,697,390 A | 12/1997 | Garrison et al. | |
| 5,711,935 A | 1/1998 | Hill et al. | |
| 5,718,251 A | 2/1998 | Gray et al. | |
| 5,755,243 A | 5/1998 | Roberts et al. | |
| 5,760,117 A | 6/1998 | Chen | |
| 5,765,576 A | 6/1998 | Dolan et al. | |
| 5,787,758 A | 8/1998 | Sheldon | |
| 5,845,652 A | 12/1998 | Tseng et al. | |
| 5,848,600 A | 12/1998 | Bacino et al. | |
| 5,884,639 A | 3/1999 | Chen | |
| 5,911,228 A | 6/1999 | Curtis et al. | |
| 5,918,609 A | 7/1999 | Tsao et al. | |
| 5,962,572 A | 10/1999 | Chen | |
| 5,967,153 A | 10/1999 | Mitha et al. | |
| 5,988,444 A | 11/1999 | Williams et al. | |
| 5,998,431 A | 12/1999 | Tsend et al. | |
| 6,003,525 A | 12/1999 | Katz | |
| 6,027,592 A | 2/2000 | Tseng et al. | |
| 6,080,481 A | 6/2000 | Ochs et al. | |
| 6,083,208 A | 7/2000 | Modak et al. | |
| 6,148,830 A | 11/2000 | Chen | |
| 6,161,555 A | 12/2000 | Chen | |
| 6,192,896 B1 | 2/2001 | Tsao et al. | |
| 6,545,077 B2 * | 4/2003 | Hill et al. | ............... 524/277 |

* cited by examiner

Primary Examiner—David W. Wu
Assistant Examiner—Rip A. Lee

(57) ABSTRACT

Various monofilament dental tapes with substantive coatings including: solutions of block copolymers and non-ionic surfactants, melt emulsions of waxes emulsified in surfactants and inverse melt emulsions of surfactants emulsified in a continuous wax phase, and their methods of manufacture are described.

45 Claims, No Drawings

MONOFILAMENT DENTAL TAPES WITH SUBSTANTIVE COATINGS

CROSS-REFERENCE TO RELATED APPLICATIONS

This application is a continuation of application Ser. No. 09/935,920, filed Aug. 23, 2001, now U.S. Pat. No. 6,545,077. That application claims priority from the following copending U.S. Provisional Patent Applications—U.S. Ser. Nos. 60/227,244, 60/227,255 and 60/227,433, each filed Aug. 23, 2000, the disclosures of which are hereby incorporated herein by reference.

BACKGROUND OF THE INVENTION

Monofilament dental tapes traditionally have focused on improving their primary consumer benefits of reduced "shredding" and reduced breakage during flossing while falling short on a range of product attributes generally associated with various releasable coatings applied to these monofilament tapes. These coating-related attributes included: hi-impact flavor, mouth feel, cleaning and "hand" of the coated tape. These attributes generally require coatings at from between about 20% by weight of the monofilament tape and about 120% by weight of the tape.

Monofilament interproximal devices are described and claimed in: U.S. Pat. Nos. Re 35,439; 3,800,812; 4,974,615; 5,760,117; 5,433,226; 5,479,952; 5,503,842; 5,755,243; 5,845,652; 5,884,639; 5,918,609; 5,962,572; 5,998,431; 6,003,525; 6,083,208; 6,148,830; 6,161,555; and 6,027,592, the disclosures of which are hereby incorporated herein by reference. These dental tapes generally have serious shortcomings in gentleness, in delivering coatings during flossing and in being handled easily and conveniently during flossing.

Polytetrafluoroethylene (PTFE) based interproxunal devices are described in: U.S. Pat. Nos. 5,209,251; 5,033,488; 5,518,012; 5,911,228; 5,220,932; 4,776,358; 5,718,251; 5,848,600; 5,878,758; and 5,765,576. To date, no commercial versions of these tapes have been coated effectively and cannot be used to deliver active ingredients, interproximally and subgingivally during flossing. Handling during flossing Is difficult. Most have to be folded to provide a consumer acceptable edge. Many are plagued with serious dimensional inconsistency problems, as well.

Most monofilament tapes and particularly the PTFE tapes are difficult to coat with "releasable coatings" at these relatively high levels, particularly when the coatings are required to be substantially free from flaking. Copending Provisional Application Ser. No. 60/263,220 is directed to crystalline-free releasable coatings for PTFE and other monofilament tapes that are substantially free from flaking. The teachings of this application are incorporated herein by reference.

Heretofore, coatings for dental flosses and dental tapes have traditionally been comprised of microcrystalline wax and a small amount of flavor. Occasionally trace amounts of "active ingredients" such as fluoride, CPC or triclosan are added. The content of each of these additives in the coating is limited to the solubility of the desired ingredients in the wax. An additional limitation of this traditional coating approach is that the flavor remains trapped inside the wax and is not available to the oral cavity or interproximal spaces during flossing. Even if the wax is mechanically removed from the floss or tape by flossing very little of the wax-trapped ingredient content makes contact with the oral cavity. In spite of the great sensitivity of taste buds and olfactory nerves, these "trapped" flavors are barely perceptible.

Hill et al. disclose a series of coating agents for multifilament dental flosses as distinguished from monofilament tapes (see U.S. Pat. Nos. 4,911,927; 5,057,310; 5,098,711; 5,165,913 and 5,711,935). These coating agents basically rely on emulsifiable ingredient consisting of a suitable surfactant, such as a poloxamer (Pluronic F-127) and a "coating agent" which is insoluble in, but emulsifiable by the surfactant in its molten state. These coating agents are typically very non-polar materials such as silicones (PDMS) or microcrystalline paraffin waxes. The teachings of the Hill, et al. patents are incorporated herein by reference.

Despite the utility of the Hill et al. coatings, their multi-functionality and commercial use in major brands and specialty professional multifilament flosses, the greatest draw-back of these melt-emulsion systems is the inherent viscosity characteristic of any emulsion, especially melt emulsions. These high viscosities necessitate a manufacturing process requiring specialized equipment to force the high viscosity melt either down into the multifilaments of the floss by means of "compression loading".

There are also many references and commercial embodiments of the use of so-called water soluble waxes, primarily high molecular weight polyethylene glycols (PEGs), to coat dental flosses and tapes. The primary function of the PEG is to serve as a saliva soluble carrier for small amounts of flavor and other additives. The advantage of a PEG coating is that its melt viscosity is low and low levels of coating can be added with very simple mechanisms requiring little need for attention by an operator. The most common of these is a simple rolling wheel, the lower one-third of which is immersed in the molten PEG, and the floss or tape is pulled across the top of the wheel, thereby picking up a small quantity of the molten PEG coating agent.

There are many shortcomings of the simple water-soluble wax (PEG) coated flosses and tapes. Among them:
(1) The products are slick and thus hard to hold (hand feel);
(2) The products lack surfactancy, i.e. the ability to clean in the interproximal spaces;
(3) The products have low coating loads due to the poor adhesion, or if thick layers or loads are applied, they bind poorly to the tape or filament surfaces and flake off easily in product manufacture, packaging and consumer use;
(4) The products use water soluble waxes which will solubilize in only a limited range, or limited quantities, of ingredients, since it has no polarity or surfactant properties;
(5) The products have no ability to promote a pleasant mouth feel as do the coatings references in the Hill et al. patents.

SUMMARY OF THE INVENTION

The present invention is directed to substantive coatings for monofilament tapes that are neither described nor suggested by the noncrystalline coatings described in copending Provisional Patent Application Ser. No. 60/263,220. These substantive coatings for monofilament tapes comprise:
(1) melt solutions of block copolymers and non-ionic surfactant polyethylene glycols in ratios from between about 80:20 and about 20:80;
(2) melt emulsions of chemotherapeutic ingredients coated on the tape at from between about 30 and 120 mg/yd containing a high percentage of surfactants as the continuous phase and a surface energy modifying level of a wax as the discontinuous phase including: microcrystalline, petroleum, bees wax, polyethylene, carnauba other natural waxes and combinations thereof; and
(3) inverse melt emulsions of surfactant in a continuous phase of wax, where the ratio of wax to surfactant is from between about 99:1 and about 60:40.

One preferred embodiment of the present invention comprises the various substantive coatings for monofilament dental tapes described herein.

Other preferred embodiments of the invention comprise the various processes for coating monofilament dental tapes with substantive coatings described herein.

A further preferred embodiment of the invention comprises the monofilament dental tapes which include a wide range of substantive coatings, as taught herein.

These and other embodiments of the invention are described in detail below.

DETAILED DESCRIPTION OF THE PREFERRED EMBODIMENTS

A: Monofilament Tape Coatings Comprising Solutions of Block Copolymers and Nonionic Surfactant Polyethylene Glycols:

It has been found that certain solution coated monofilament dental tapes of the present invention surprisingly have a high level of flavor released when flossing, and furthermore, exhibit unexpected flexibility and attachment during subsequent winding steps. Block co-polymers, such as PLURONIC® F-127, are formulated in a range of from 48 to 90 percent by melting along with 47 to 7 percent by weight of the non-ionic surfactant polyethylene glycol 1450. Flavors are utilized from 2 to 17 percent by weight.

The melt solution coated monofilament dental tapes of the present Invention surprisingly have a high level of flavor released when flossing, while exhibiting unexpected flexibility and attachment during subsequent winding steps. In contrast, coatings utilizing a single non-Ionic surfactant have exhibited less than desirable retention on the dental tape with extensive flaking off.

A general purpose "chemical base" is first formed from a solution of a water-soluble wax (PEG or similar substances) and a PEG-soluble surfactant (such as a poloxamer typified by PLURONIC® F-127 supplied by BASF). This is made by melting and combining the two ingredients with a ratio ranging from 90:10 to 10:90. Preferably, the ratio of PEG to surfactant ranges from 80:20 to 20:80. The range will vary dependent upon the nature and chemistry of the other ingredients required, the flexibility of the finished coating desired, and the processing equipment chosen. Dental flosses and dental tapes will also require different variations within the specified ranges to accommodate the different surface free energies and surface areas.

To the above solution or "chemical base", one or more of the following multi-functional ingredients are added. The value of this invention is seen in the increased quantities, number of ingredients and variety of chemistries accommodated by the unique solution of neutral and surfactant water-soluble polymers.

(1) Mouth feel agents such as carboxy methyl cellulose (CMC), hydroxypropylcellulose, natural gums, resins and the like;
(2) Flavoring and sweetening agents;
(3) Soft abrasives which are suspendable in the low viscosity solutions, including silica gels, porous calcium carbonates, and natural abrasives such as rice flours, bran, corn powders, and the like;
(4) Antimicrobials such as CPC, triclosan, metronidazole, chlorhexidine digluconate, and the like;
(5) Fluoride sources such as Sodium Fluoride, Stannous Fluoride, and the like;
(6) Tartar control agents;
(7) NSAIDs and MMP inhibitors;
(8) Soluble emulsifying agents such as ethylene vinyl alcohol copolymers or other copolymers soluble in the "chemical base";
(9) Colorants and opacifiers.

This embodiment of the present invention will be further illustrated with reference to Examples 1 and 2 which will aid in the understanding of the present invention, but which are not to be construed as limitations thereof. All percentages reported herein, unless otherwise specified, are percent by weight. All temperatures are expressed in degrees Celsius.

EXAMPLE 1

The block co-polymer Pluronic F-127, at 3040 grams, was melted with stirring at 90° C. The non-ionic surfactant polyethylene glycol (PEG) 1450, at 1545 grams was added with stirring at a rate to form an emulsion-free solution. Insoluble saccharin, 115 grams, was added to the solution with stirring until dissolved. The solution was cooled to 75–80° C. and 300 grams of a peppermint flavor added with stirring. This solution was flaked after cooling to produce the final useable product. When dental tape is ready to be coated, the flakes are re-melted and the coating applied as described in detail below.

The solution was coated on an elastomeric tape FIBACLEAN® by Perident Company as described in copending application Ser. No. 09/330,491, incorporated herein by reference) bypassing the tape through a bath of the solution at 90° C. and excess quantity removed by means of a pair ofheated rollers set at 0.004 inches separation. The tape, with the solution having cooled, was then taken up on standard take-up winders. The resultant coating was flexible, had excellent taste properties and provided a load of about 15% of the virgin tape.

EXAMPLE 2

To the melt solution of Example 1 is added 100 grams of hydroxymethyl cellulose, 400 grams of rice powder (passing through 70 mesh) and 50 grams of cetyl pyridinium chloride (CPC). The tape was coated in a manner like Example 1 except the rollers were set at 0.005 inches apart. This resulted In a coating equal to about 30% of the virgin tape weight again with excellent flexibility and taste while containing the CPC and rice powder.

B: Monofilament Tape Coatings Comprising Melt Emulsions of Wax in a Continuous Surfactant Phase:

The coated monofilament tapes of this embodiment of the present invention can contain from about 30–120 mg of total chemotherapeutic ingredient(s) per yard on a standard 0.050 inch wide tape. Other widths will produce a correspondingly higher or lower range of loads as the width varies. Depending on the process parameters and formulation of the coating, the thickness of active ingredient on each side of the tape can vary from 0.001 to 0.005 inches. More typically, the thickness will range from between about 0.0015 and 0.0035 inches.

Materials with a very low surface free energy are described in layman's terms as "nothing sticks to it". Such is the case with prototypical monofilament tapes including PTFE-TEFLON® tapes. Other monofilament polymers such as polyethylene, polypropylene and various elastomers as described in the copending Provisional Patent Application Ser. No. 60/263,220 have a similar description and slightly higher surface free energy than TEFLON®, but still low enough that adhesion is difficult for normally very adhesive substances. Given the low surface free energies of the various monofilament tape polymers, it is surprising that the melt-emulsions described in the referenced Hill patents can be used in this invention substantially free from "flaking off" either in process, packaging or user handling It is also unexpected that these melt-emulsion coatings also avoid the pitfall of inconsistent and patchy adherence. Heretofore, only very thin coatings with microcrystalline wax have been achieved in an ineffective attempt to reduce the tendency to slip in the hand and fingers.

It would be unobvious to one skilled in the art that a substantial melt emulsion coating of ingredients with a high percentage of surfactants (which normally cause solids to release from each other) could be made to adhere quite firmly to a monofilament tape, and remain substantially free of flaking. It is often advantageous to modify the surface free energy of these melt emulsions by incorporating specific "surface energy modifying" coating agents into the melt emulsions, either alone or with other coating agents such as polydimethyl-siloxane.

The use of various waxes such as microcrystalline petroleum waxes, bees wax, polyethylene waxes, carnauba and other natural waxes serves well in the matching of the surface energies of the tape polymer and the melt emulsion formulation. This matching of the surface energy is a major function in reducing or eliminating the "flaking off" and allowing the adherence of the agents to the tape through the manufacturing processes, packaging and handling by the user until it is released during flossing by the friction against the interproximal tooth surfaces and/or softened and dissolved by the crevicular and salival fluids.

The process for achieving the substantive coating of monofilament dental tapes with melt emulsions is itself a surprise, even to those well experienced in loading chemotherapeutic agents into multifilament yearns according to the teachings of Hill, et al. since the structure of the monofilament dental tape resists the compression loading of the melt emulsion by pushing it into the spread out interstitial spaces between the multifilaments, the process of the present invention would be more appropriately described as "pressure adhesion" where materials that normally do not stick or adhere together are induced by the pressures described herein to adhere to the monofilament tape.

The equipment and principles described in the various Hill, et al. patents are for the purpose of (1) spreading the filaments in the floss bundle, (2) incorporating as much melt emulsion as is feasible and finally, (3) forcing the maximum amount of melt emulsion between the filaments and surrounding each individual filament by compression loading with heated rollers with a gap of fixed dimensions to finally spread the filaments to their widest point. Upon leaving the rollers, the filament bundle re-assumes its round cross section and passes through a cooling section before being wound on cylinders.

The result of this process is that most of the melt emulsion agents are compressed "inside" the fiber bundle so that the outside feels dry and un-coated to the touch. In the case of multi-filament flosses, this spreading is quite visible at each stage of the compression loading and especially so in the nip of the heated roller where the bundle is several times wider on the exit side than on the entrance side and the "track" of melt-emulsion removed from the rollers and transferred to the floss is several times wider than the exiting bundle of fibers after they re-assume their round cross section.

In the case of the monofilament tapes, there is clearly no way to "spread" parts of the tape apart by compression without destroying the integrity of the tape. Further, there is no purpose to the repeated exposure to contact with the melt-emulsion. However, when the manufacturing process described in Hill et al., and especially its most preferred commercial embodiment—the use of heated compression loading rollers—is modified as described herein, there is in fact a phenomenon which can only be described as "pressure adhesion." There appears to be no physical room for compression of the monofilament tapes, nor any visible evidence of compression or flattening of the tapes, yet the load is adhered beyond what one would expect.

An excess (called a "bubble") of melt-emulsion is maintained at the nip of heated rollers (typically 100° C.–200° C.) by pumping and spreading the melt emulsion directly to the upper roller at a rate equal to or greater than the uptake on the monofilament tape as it passes through. This excess at the nip feeds the contacting lower roller as well as providing the reservoir for the pressure adhesion coating the incoming monofilament tape. The monofilament tape (in a typical case the tape is 0.0025 inches thick) is fed directly into the nip, passing through the "bubble" of melt-emulsion. The rollers are set at 0.002±0.0002 inches and maintained at that dimension under a roller face pressure of 1500 pounds. Other thickness monofilament tapes are accommodated by proportional adjustment of the roller gap.

Typically, in the use of heated rollers to coat tapes such as video tape or films used in medicament patches (such as nicotine or nitroglycerin) the roller gap is set equal to the sum of the tape/film thickness plus the desired coating thickness on each side. By setting a doctor blade on each roller (one or both rollers, depending on whether a one-side or two-side coat is desired) just before the nip and just after the introduction of the ingredient at a distance equal to the desired coating thickness, a very accurate amount of coating agent is uniformly applied by a process often called "doctoring on". In such a case the tape or film is said to "doctor off" the ingredient which coats the substrate and the exit side of the roller is wiped clean.

Using such a "doctoring off" method, as one skilled in the art would naturally tend to do, does not effectively produce as satisfactory a product when the tape is a low surface free energy material, i.e., a monofilament dental tape and the coating agent contains a large percentage of surfactant. By introducing a tremendous, almost incalculable amount of "adhesive" pressure at the nip with a roller gap actually narrower than the finished product, and applying an extremely viscous coating agent only possible with melt-emulsion physics, the inherent tendency of the low surface energy monofilament substrate to reject the high surfactant coating agent is overcome and pressure adhesive coatings are unexpectedly achieved at the surface of the various monofilament tapes.

The skilled artisan will appreciate the fact that the use of melt emulsion with "high tack" properties, or monofilament tapes constructed from high surface free energy polymers, would allow for production of satisfactory products with much lower roller pressures. Such a process falls within the scope of this embodiment of the invention. Heated rollers capable of generating pressures of 100 to 4000 pounds and roller gap settings from just smaller than the virgin monofilament tape to just smaller than the combined thickness of the virgin monofilament tape and added melt emulsion are within the teachings of this invention.

The mechanism by which this pressure adhesion exactly happens is not clearly understood, but one can postulate some mechanisms which helps one skilled in the art to develop variations on the examples cited here. However, the postulated mechanisms should not be construed to limit the present invention to the specifics of the proposed mechanisms.

From the examples below, it is evident that the finished product thickness (virgin monofilament tape+two sides coated) is several times greater than the roller gap through which the tape just passed. There is the possibility, of course, that the rollers are indeed spread further apart by the soft polymeric monofilament tape and or the fluid melt-emulsion. Accounting for more than three times the gap setting is difficult, since the phenomenon is observed when only one strand of monofilament tape (0.050 inches wide) is passed through the rollers. It is difficult to measure the gap "on the fly" since any calibrated "feeler gauge" metal would indeed force the rollers apart against 1500 pounds of pressure. But virgin monofilament tape inserted between the rollers outside the deckles (therefore not contacted by the melt-emulsion) while tape is being loaded between the deckles, exhibits the same degree of friction that it exhibits when the loading process is not underway. Were the gap actually spread from 0.002 to 0.006 inches, the monofilament tape would have almost no friction in the gap. Further, the melt-emulsion is a thixotropic fluid, thinning under shear. One would expect the thixotropic fluid to thin out to the point of exhaustion from the surface of the monofilament tape before clearing the nip. It may be that the shear-thinned melt-emulsion flows quickly back on the monofilament tape, leaving the exit side of the rollers with a stripe that is free of melt-emulsion exactly the width of the entering virgin monofilament tape.

One plausible postulate for the unusual binding ability imposed by the pressure adhesion process of this invention is that the combination of elevated temperatures (typically 100° C.–200° C.) and the pressures generated at the nip drives one of the fluid phases (either the discontinuous or the continuous phase) into the microscopic and submicroscopic crevices and fissures present in any polymeric monofilament substance. Thus trapped, the effective surface free energy of the monofilament tape is increased, and perhaps even matches that of the relatively thick coat of melt emulsion one finds at the end of the process. Such would give the coating a surface to which it would bind, much as a primer which penetrates the wood is used before painting. Such a mechanism would be well described as "pressure induced adhesion" and/or "pressure-adhesion" as used herein.

This embodiment of the present invention will be further illustrated with reference to the following examples which are not to be construed as limitations thereof. All percentages reported herein, unless otherwise specified, are percent by weight.

In the following examples, the tape was FIBACLEAN® from the Perident Company with a thickness of 0.0025 inches and a width of 0.050 in. See for example, PCT Publication No. WO 98/50607 and U.S. Ser. No. 09/330,491, the disclosure of which are incoiporated herein by reference. The heated rollers were set with a gap of 0.002"–0.0002", temperatures ranged from 110° C.–150° C. depending on the melt-emulsion viscosity requirements.

EXAMPLE 3

Chlorhexidine Chemotherapeutic Tape

| Melt-Emulsion Ingredients | % w/w | Load mg/yd | Final Thickness |
|---|---|---|---|
| Pluronic F-127 | 56.52 | | |
| 2.5 MM cs PDMS[(1)] | 6.28 | | |
| PEG 1450 | 7.0 | | |
| Mic. Wax ML 445 | 22.4 | 53.2 | 0.005 in. |
| Saccharin, insol | 1.8 | | |

-continued

| Melt-Emulsion Ingredients | % w/w | Load mg/yd | Final Thickness |
|---|---|---|---|
| Flavor | 5.4 | | |
| Chlorhexidine base | 0.6 | | |

[(1)]PDMS = polydimethylsiloxane at 2,5000,00 cs viscosity combined with the PLURONIC ® F-127 in the form of an ULTRAMULSION ® as described in various Hill patents.

(1) PDMS=polydimethylsiloxane at 2,500,00 cs viscosity combined with the PLURONIC® F-127 in the form of an ULTRAMULSION® as described in various Hill patents.

EXAMPLE 4

Stannous Fluoride Chemotherapeutic Tape

| Melt-Emulsion Ingredients | % w/w | Load mg/yd | Final Thickness |
|---|---|---|---|
| Pluronic F-127 | 40.23 | | |
| 2.5 MM cs PDMS[(1)] | 4.47 | | |
| PEG 1450 | 7.0 | 77.2 | 0.005 in. |
| Silica, toothpaste grade | 10.8 | | |
| Wax ML 445 | 24.4 | | |
| Saccharin, insol | 2.1 | | |
| Flavor | 6.2 | | |
| Stannous Fluoride | 4.8 | | |

EXAMPLE 5

Soft Abrasive Cleaning Chemotherapeutic Tape

| Melt-Emulsion Ingredients | % w/w | Load mg/yd | Final Thickness |
|---|---|---|---|
| Pluronic F-127 | 43.1 | | |
| 1000 cs PDMS[(2)] | 10.0 | | |
| PEG 1450 | 7.0 | | |
| Mic. Wax ML 445 | -0- | 106 mg/yd | 0.0065 in |
| Saccharin, sodium | 2.3 | | |
| Flavor | 8.6 | | |
| Propyl gallate | 0.1 | | |
| Silica (Sident 10) | 10.0 | | |
| Rice Flour (35–70 mesh) | 10.0 | | |
| Pumice 2F | 0.5 | | |
| Sodium Fluoride | 0.39 | | |

[(2)]PDMS added directly to the melt-emulsion

EXAMPLE 6

Evaluation of Practical Bonding of the Chemotherapeutic
Coating in Example #4

Illustrative of the unusual ability of this product and process to hold the active ingredient coating tenaciously to the low surface energy tape is an experiment whereby the tape in Example #4 was commercially "stuffed" into a single dose packet by a mechanism patented by Arthur P. Corella and commercially practiced by APC Industries, Burbank, Calif. In this form-fill-seal process, the tape is pulled into a 22 inch cylinder with a ¼ inch bore. Then the tape is compressed to the bottom with a TEFLON plunger where the tape assumes a tight, accordion pleat shaped "knot" about ⅜ inch long. It is then expelled into the formed packet. Finally, packet is sealed at the top just prior to the next cycle of the plunger. Absent the advantages of this invention, one would expect a substantial portion of the tape coating to flake off.

A chemical assay of the fluoride content of the original chemotherapeutic tape (1) as it was removed from the take-up winder package of the loading mechanism was compared with (2) the tape removed from the single dose packets.

| Fluoride level mg/yd | | Average loss after |
|---|---|---|
| (a) Before Packaging | (b) After Packaging | accordion folding packaging, unfolding and removal |
| 0.83 | 0.79 | 4.8% |

C: Monofilament Tape Coating Comprising an Inverse Melt Emulsion

The quantity of the surfactant or surfactant solution is less then that of the wax, so that any emulsion which forms has a continuous phase of insoluble wax surrounding a lesser quantity of spheres of the surfactant, or discontinuous phase. The ratio of wax (continuous phase) to surfactant (discontinuous phase) can be from 99:1 to 60:40 but more typically from 80:20 to 98:2 and preferable from 85:15 to 97:3.

The molten mixture is then emulsified by any suitable high shear mechanical device. One such common devise is a Greerco Homogenizer, which has the advantage of convenient size and portability for use in various melt tanks. However many high shear devices, including waxing blenders from the kitchen or in-line emulsifiers form the mayonnaise industry would also be suitable. The inverse emulsion, where the wax is on the outside, encapsulating the surfactant or surfactant solution, may in certain embodiments, coalesce and the finely divided spheres of surfactant re-aggregate into two distinct layers. In the manufacturing process, this is easily overcome by keeping the mechanical shear device running in the melt tank, and the discontinuous phase can only re-aggregate after the tape has cooled.

The surfactant chosen must be suitable for use in the oral cavity and meltable as liquid at the melt temperature conditions usually employed by manufacturing equipment for wax coating dental tapes and flosses. Further, it must be essentially insoluble in the wax itself. This is to prevent two formulations of a wax solution whose properties are greatly modified by the additives and either makes an unsuitable soft, slick or gummy coating, or cannot be processed on ordinary equipment. Further, an insoluble-in-wax surfactant does not make the wax itself soluble or dispensable in water, saliva and the like. For the wax to be dispersable in saliva, one must conform the exact opposite teachings of two previously referenced Hill et al. patents and disclosures.

It is a further advantage for this invention if the selected surfactant is capable of solubilizing other desired ingredients flavors and saccharin or other sweeteners. Those surfactants which, by solubility and equilibrium principles, hold the flavorants primarily within. The surfactants and spheres of the emulsion are preferred. Many surfactants will meet these requirements, especially non-ionic surfactants. The poloxamer class of surfactants, block copolymers of ethylene oxide and propylene oxide, are particularly similar, non-surfactant molecules such as discontinuous phase downward. Conversely, surfactants which have high surfactant properties and are soluble in the poloxamer but not in the wax may be added to the poloxamer to increase the surfactant properties of the discontinuous phase.

While not limiting the scope of this invention to the proposed mechanisms of action, the beneficial nature of monofilament dental tapes coated with inverse emulsions this invention are thought to be due to (1) The insolubility in water, saliva and oral fluids of the continuous phase (i.e., the wax), (2) The additives of flavorants, sweeteners and the like are not "lost" to the sensory organs by reason of this dissolution into the insoluble wax and (3) The "make and break" of the spheres just below the surface of the insoluble wax as the tape or floss is worked into the interproximal spaces and against the tooth surfaces. This physical disruption releases small amounts of the derived agents into the oral cavity, producing flavor perceptions not deliverable by the standard methods of adding flavorants directly into the insoluble wax.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. Monofilament dental tapes coated with a substantive coating comprising:
    a melt solution comprising a water soluble wax and block copolymers of ethylene oxide and propylene oxide in ratios from between about 90:10 to 10:90; and
    at least one multi-functional ingredient, wherein the coating remains flexible and substantially free from flaking prior to use.

2. The monofilament dental tapes of claim 1, wherein the water soluble wax comprises a polyethylene glycol.

3. The monofilament dental tapes of claim 2, wherein the polyethylene glycol is polyethylene glycol 1450.

4. The monofilament dental tapes of claim 1, wherein the block copolymer is a poloxamer.

5. The monofilament dental tapes of claim 4, wherein the poloxamer is a nonionic polyoxyethylene-polyoxypropylene block co-polymer.

6. The monofilament dental tapes of claim 1, wherein the ratio of the water soluble wax to the block copolymers is from between about 80:20 to 20:80.

7. The monofilament dental tapes of claim 1, wherein the at least one multi-functional ingredient is selected from the group consisting of mouth feel agents, flavoring agents, sweetening agents soft abrasive antimicrobials, fluoride sources, tartar control agents, NSAID inhibitors, MMP inhibitors, soluble emulsifying agents, colorants and opacifiers.

8. The monofilament dental tapes of claim 7, wherein the mouth feel agents are selected from the group consisting of carboxy methyl cellulose, hydroxypropylcellulose, natural gums, reams and combinations thereof.

9. The monofilament dental tapes of claim 7, wherein the flavoring agent is peppermint flavored.

10. The monofilament dental tapes of claim 7, wherein the flavoring agent is utilized from about 2 to 17 weight %.

11. The monofilament dental tapes of claim 7, wherein the sweetening agents comprise saccharin or a salt thereof.

12. The monofilament dental tapes of claim 7, wherein the soft abrasives are selected from the group consisting of silica gels, porous calcium carbonates, natural abrasives and combinations thereof.

13. The monofilament dental tapes of claim 12, wherein the natural abrasives are selected from the group consisting of rice flours, bran, corn powders and combinations thereof.

14. The monofilament dental tapes of claim 7, wherein the antimicrobials are selected from the group consisting of cetyl pyridinium chloride, triclosan, metronidazole, chlorhexidine digluconate and combinations thereof.

15. The monofilament dental tapes of claim 7, wherein the fluoride sources are selected from the group consisting of sodium fluoride, stannous fluoride and combinations thereof.

16. The monofilament dental tapes of claim 7, wherein the soluble emulsifying agents comprise ethylene vinyl alcohol copolymers.

17. A method of coating monofilament dental tapes with the substantive coating of claim 1 comprising:

forming a melt solution comprising a water soluble wax and block copolymers of ethylene oxide and propylene oxide in ratios from between about 90:10 to 10:90; and passing a virgin monofilament dental tape through the melt solution.

18. The method of claim 17, further comprising removing excess melt solution from the coated monofilament dental tape with heated rollers.

19. The method of claim 17, wherein the coated monofilament dental tape has a load of about 15–30% of the virgin monofilament dental tape.

20. Monofilament dental tapes coated with a substantive coating comprising:

a melt emulsion comprising at least one surfactant, at least one surface energy modifying agent, and a coating agent, wherein the ratio of surfactant to surface energy modifying agent as from between about 2:1 to about 4:1, wherein the coating remains flexible and substantially free from flaking prior to use.

21. The monofilament dental tapes of claim 20, wherein the coating agent comprises polydimethylsiloxane.

22. The monofilament dental tapes of claim 20, wherein the surface energy modifying agent is selected from the group consisting of microcrystalline wax, petroleum wax, bees wax, carnauba wax, other natural waxes, and combinations thereof.

23. The monofilament dental tapes of claim 20, wherein the surfactant comprises a poloxamer.

24. The monofilament dental tapes of claim 23, wherein the poloxamer is a nonionic polyoxyethylene-polyoxypropylene block co-polymer.

25. The monofilament dental tapes of claim 20, further comprising an active ingredient.

26. The monofilament dental tapes of claim 25, wherein the active ingredient is a chemotherapeutic ingredient.

27. The monofilament dental tapes of claim 26, wherein the chemotherapeutic ingredient is present in an amount of about 30–120 mg per yard of the monofilament dental tape when the monofilament dental tape is about 0.050 inch wide.

28. The monofilament dental tapes of claim 25, wherein the active ingredient has a thickness on each side of the monofilament dental tapes of about 0.001–0.005 inches.

29. The monofilament dental tapes of claim 20, further comprising at least one selected from the consisting of: mouth feel agents, flavoring agent, sweetening agent, antimicrobials, fluoride sources, tartar control agents, NSAID inhibitors, MMP inhibitors, soluble emulsifying agents, colorants and opacifiers.

30. The monofilament dental tapes of claim 20, wherein the monofilament dental tapes have a surface free energy similar to that of polytetrafluoroethylene.

31. The monofilament dental tapes of claim 20, wherein the melt emulsion has a consistent adherence to the monofilament dental tapes.

32. The monofilament dental tapes of claim 20, wherein the melt emulsion has a surface energy approximately equal to the surface energy of the monofilament dental tapes.

33. A method of coating monofilament dental tapes with the melt emulsion of claim 20 comprising:

providing a virgin monofilament dental tape; and introducing the monofilament dental tape to a pressure roller having a nip, wherein the nip has bubble comprising a melt emulsion comprising at least one surfactant and at least one surface energy modifying agent, wherein the ratio of surfactant to surface energy modifying agent is from between about 2:1 to about 4:1, and wherein the melt emulsion is maintained on the monofilament dental tape by pressure adhesion.

34. The method of claim 33, wherein the monofilament dental tape is fed into the nip.

35. The method of claim 33, wherein the monofilament dental tape is introduced into a pair of rollers heated to a temperature up to about 200° C.

36. The method of claim 35, wherein the pair of rollers is spaced about 0.002 inches apart while the monofilament dental tape is introduced to the pair of rollers, and wherein the virgin monofilament dental tape has a thickness greater than about 0.002 inches.

37. The method of claim 33, wherein the monofilament dental tape has more than one coated side.

38. Monofilament dental tapes coated with a substantive coating comprising:

an inverse melt emulsion comprising a wax and a surfactant in a ratio from about 80:20 to 98:2, wherein the wax encapsulates the surfactant; and at least one multi-functional ingredient, wherein the coating remains flexible and substantially free from flaking prior to use.

39. The monofilament dental tapes of claim 38, wherein the wax is selected from the group consisting of microcrystalline wax, petroleum wax, bees wax, carnauba wax, other natural waxes and combinations thereof.

40. The monofilament dental tapes of claim 38, wherein the surfactant comprises a non-ionic surfactant.

41. The monofilament dental tapes of claim 38, wherein the surfactant comprises a poloxamer.

42. The monofilament dental tapes of claim 41, wherein the poloxamer is a nonionic polyoxyethylene-polypropylene block co-polymer.

43. The monofilament dental tapes of claim 41, wherein the poloxamer further comprises a surfactant with high surfactant properties.

44. The monofilament dental tapes of claim 38, wherein the surfactant is suitable for use in the oral cavity and is insoluble in the wax.

45. The monofilament dental tapes of claim 38, wherein the surfactant is capable of solubilizing the at least one multi-functional ingredient.

* * * * *